United States Patent
Wolfe

(10) Patent No.: US 10,107,437 B2
(45) Date of Patent: Oct. 23, 2018

(54) TOOLING FRIENDLY ADAPTER FOR INSERTION PROBE ACCESS

(71) Applicant: Mustang Sampling LLC, Ravenswood, WV (US)

(72) Inventor: Nicholas S. Wolfe, Ravenswood, WV (US)

(73) Assignee: Mustang Sampling LLC, Ravenswood, WV (US)

( * ) Notice: Subject to any disclaimer, the term of this patent is extended or adjusted under 35 U.S.C. 154(b) by 217 days.

(21) Appl. No.: 15/258,227

(22) Filed: Sep. 7, 2016

(65) Prior Publication Data

US 2017/0074693 A1   Mar. 16, 2017

Related U.S. Application Data

(60) Provisional application No. 62/218,663, filed on Sep. 15, 2015.

(51) Int. Cl.
*F16L 41/14* (2006.01)
*G01N 1/22* (2006.01)
*G01N 1/20* (2006.01)

(52) U.S. Cl.
CPC ............ *F16L 41/14* (2013.01); *G01N 1/2035* (2013.01); *G01N 1/2247* (2013.01)

(58) Field of Classification Search
CPC ...... F16L 41/14; G01N 1/2035; G01N 1/2247
See application file for complete search history.

(56) References Cited

U.S. PATENT DOCUMENTS

| 3,939,713 | A | | 2/1976 | Estey |
| 3,996,124 | A | | 12/1976 | Eaton et al. |
| 4,487,080 | A | | 12/1984 | Leaseburge et al. |
| 4,821,905 | A | † | 4/1989 | Hess |
| 4,920,626 | A | | 5/1990 | Nimberger |
| 5,109,709 | A | | 5/1992 | Nimberger |
| 5,325,731 | A | | 7/1994 | Miller et al. |
| 5,531,130 | A | | 7/1996 | Welker |
| 5,936,168 | A | | 8/1999 | Welker |
| 6,539,312 | B1 | | 3/2003 | Nimberger et al. |
| 7,051,604 | B1 | * | 5/2006 | Mayeaux ............. G01N 1/2247 73/863.11 |
| D674,052 | S | † | 1/2013 | Thompson |

(Continued)

FOREIGN PATENT DOCUMENTS

WO   2014/160295 A1   10/2014

OTHER PUBLICATIONS

Mustang Sampling, LLC., "Mustang Certicollar Mounting Brackets," MSB-MCC, vol. 2.3, 2009-2016 Mustang Sampling, LLC., Ravenswood, U.S.

(Continued)

*Primary Examiner* — Hezron E Williams
*Assistant Examiner* — David Z Huang
(74) *Attorney, Agent, or Firm* — Cahn & Samuels, LLP

(57) ABSTRACT

An insertion probe adapter for fluid sample extraction from a pipeline for mounting of an overlying housing element is illustrated and described. The invention permits disengagement of an insertion probe from the body of the probe adapter without disassembling the body from the pipeline and without disassembling the overlying housing element from the body.

16 Claims, 5 Drawing Sheets

(56) References Cited

U.S. PATENT DOCUMENTS

| | | |
|---|---|---|
| 9,018,608 B1 | 4/2015 | Mayeaux |
| 2002/0102130 A1 | 8/2002 | Nygren et al. |
| 2006/0117832 A1 | 6/2006 | Nakashima et al. |
| 2010/0058881 A1 | 3/2010 | Braaten |
| 2012/0325694 A1 † | 12/2012 | Thompson |
| 2017/0234777 A1 † | 8/2017 | St Amant, III |

OTHER PUBLICATIONS

The International Search Report and The Written Opinion of The International Searching Authority, PCT/US16/50726, dated Sep. 8, 2016.

\* cited by examiner
† cited by third party

TOOLING FRIENDLY ADAPTER FOR INSERTION PROBE ACCESS

FIELD OF INVENTION

The invention relates to an insertion probe adapter for mounting and removing an insertion probe from a permanently mounted probe housing enclosure associated with a pipeline sample take-off.

BACKGROUND OF THE INVENTION

In active natural gas pipeline operations sample take-off probes are located at select locations for sample extraction to monitor content quality and quantity. Conventional pipeline sample extraction probe design incorporates membrane filters at the probe extraction orifice, an elongated fluid sample communication channel, and an upper probe portion projecting from the pipeline exterior. For the purpose of isolating the probe to direct exposure of the ambient environment, the probes commonly are protected by an overlying enclosure/housing/shelter. Typically, for probe maintenance operations, for example, removal and/or replacement of membrane filters located at or on the tips of insertion probes, it is necessary to first remove the protective housing/enclosure followed by removal of the probe itself from the pipeline. Consequently, to gain access to the probe necessitates disassembly of the housing from both the pipeline and the upper portion of the probe which, in effect, increases time, labor, and costs to accomplish proper probe maintenance. As a result, additional steps of removing and reinstalling the probe housing in order to access the insertion probe is required of the field worker to uninstall and then re-install both the probe housing and the insertion probe from the pipeline each time there is a need to physically access the probe tip and the associated membrane filter.

A sample take-off assembly that permits removal of the insertion probe from the pipeline without dislodging the probe housing from its fixed location relative to the pipeline would be beneficial in reducing the labor intensive procedures currently practiced for servicing insertion probes in the gas sampling and conditioning industry.

SUMMARY OF THE INVENTION

It is an object of the present invention to overcome problems associated with the prior art.

Another object of the invention is to provide a novel insertion probe mounting adapter having improved functionality over prior art sample take-off assemblies.

Still another object of the invention is to provide a sample take-off mounting assembly that permits removal of the insertion probe from the pipeline without the need for its disassembly from the pipeline in order to remove the covered pipeline sample probe.

A further object of the invention is to provide direct access to the insertion probe from the interior of the overlying enclosure without the need for removal of the overlying probe housing enclosure when accessing the insertion probe for maintenance or replacement.

Yet another object of the invention is to reduce time and labor expenditures associated with membrane filter repair or replacement at or on the tips of insertion probes by providing a tooling friendly mounting adapter.

These and other objects are satisfied by an insertion probe adapter for fluid sample extraction from a pipeline for mounting of an overlying housing element, comprising: a body incorporating a pipe mounting flange defining an upper surface and a lower surface, a pipeline-engaging projecting stem projecting from the lower surface for securing the body to an underlying pipeline, a generally axially disposed feedthrough bore for removably retaining an insertion probe engaged therewith axially extending through the depth of the body, the upper surface of said flange providing an engaging surface for an overlying housing element including at least one fastening member disposed thereon offset from the generally axially disposed feedthrough bore for receiving and retaining the overlying housing element for mounting the housing element thereto; and said lower flange surface including at least one tool engaging flat formed by a cutout along the perimeter thereof; where an insertion probe is removable from the body without disassembling the body from the pipeline and the overlying housing element from the body, by disengaging the probe from the body while engaging a tool with said at least one tooling flat.

Certain objects of the invention are satisfied by an insertion probe feedthrough adapter comprising: a body for receiving an insertion probe and mounting an overlying enclosure, the body having a top surface and a bottom surface; a bottom portion extending axially from the bottom surface of the body for mounting an adapter; an interiorly threaded top port disposed proximate to the top surface of the body and having a first depth; and a feedthrough bore having a second depth, a central axis of the feedthrough bore coaxial and aligned with a central axis of the top port.

Still further certain objects of the invention are satisfied by the method of removing an insertion probe from a tool-engagable mounting adapter in a protective enclosure from a pipeline where the protective enclosure is mounted to the pipeline on the tool-engagable mounting adapter which is mounted to the pipeline where the tool-engagable mounting adapter features an anti-rotation tool engaging surface, the method comprising the steps of: engaging the anti-rotation tool engaging surface of the tool-engagable mounting adapter with a first tool; engaging a second tool with the insertion probe in the protective enclosure and applying rotational force thereto relative to the tool-engagable mounting adapter; and removing the insertion probe from the tool-engagable mounting adapter while preventing rotation of the tool-engagable mounting adapter relative to the underlying pipeline and overlying protective enclosure.

The probe adapter structure of the present invention facilitates membrane filter and/or insertion probe replacement by providing a substantially permanent mounting member for an associated ambient environment-isolating, probe housing. The tooling friendly probe mounting adapter of the invention includes tool receiving/gripping flats to allow the field worker to apply torqueing force to the probe relative to the adapter to prevent movement of the mounting adapter relative to the underlying pipe and overlying housing while unscrewing the insertion probe from the adapter for removal from the pipeline and housing. Having the ability to remove the insertion probe without disturbing the overlying housing relative to the underlying pipeline provides for more efficient probe maintenance operations when servicing system components. In the context of systems located in space-limited environments, such as a tanker ship or on a drilling platform, the present invention minimizes the required degree of access to the probe and dispenses with the need to separately dismount the protective enclosure before accessing the insertion probe.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the root terms "include" and/or "have", when used in this specification, specify the presence of stated features, steps, operations, elements, and/or components, but do not preclude the presence or addition of at least one other feature, step, operation, element, component, and/or groups thereof.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

In the detailed description, references to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

For definitional purposes and as used herein "mounting" includes physically contacting, permanently affixed, or releasably connected, as for example, mounting the overlying enclosure to the probe adapter. Thus, unless specified, "mounting" is intended to embrace any operationally functional connection.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

As used herein "substantially" and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings, which are shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION OF THE DRAWINGS

Figure 1:
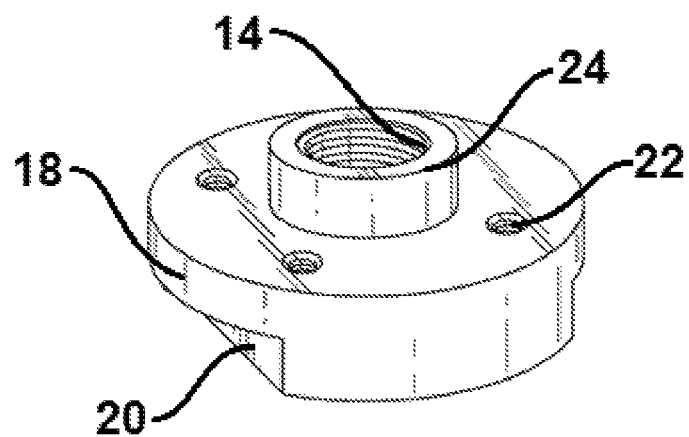
FIG. 1 is an upper perspective view of an embodiment of the insertion probe adapter according to the present invention.
Figure 2:
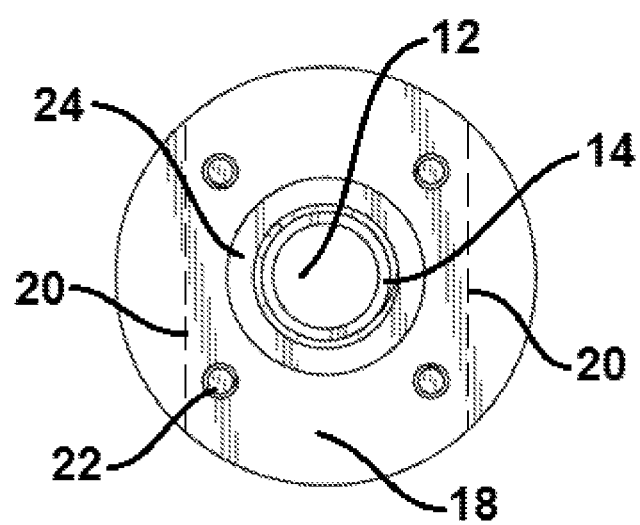
FIG. 2 is a top view of the embodiment illustrated in FIG. 1.
Figure 3:
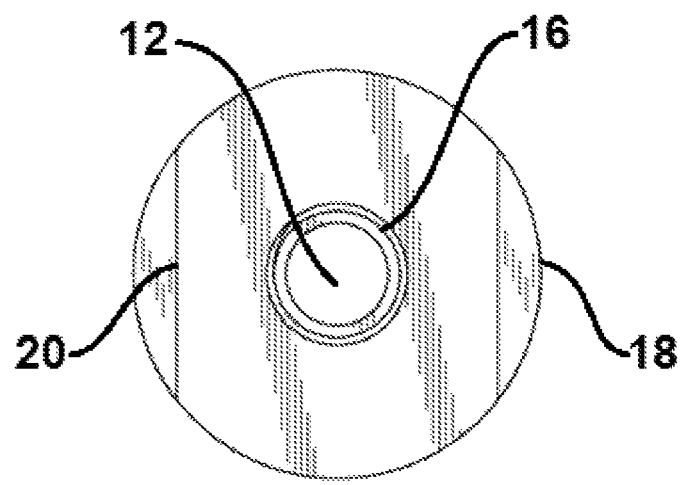
FIG. 3 is a bottom view of the embodiment illustrated in FIG. 1.
Figure 4:
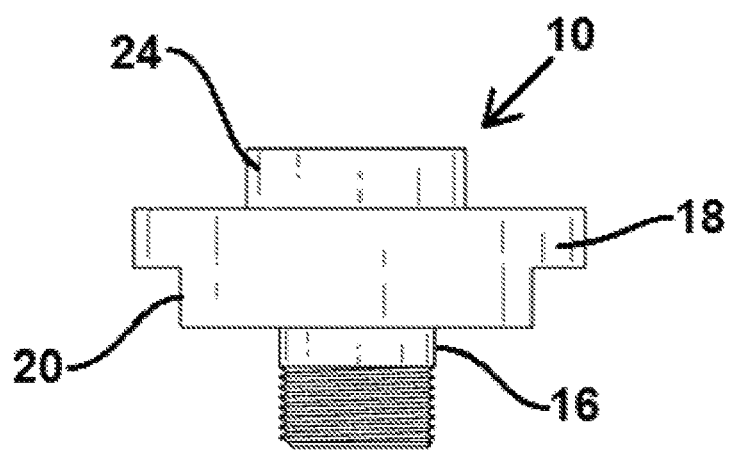
FIG. 4 is a first side view of the embodiment illustrated in FIG. 3.
Figure 5:
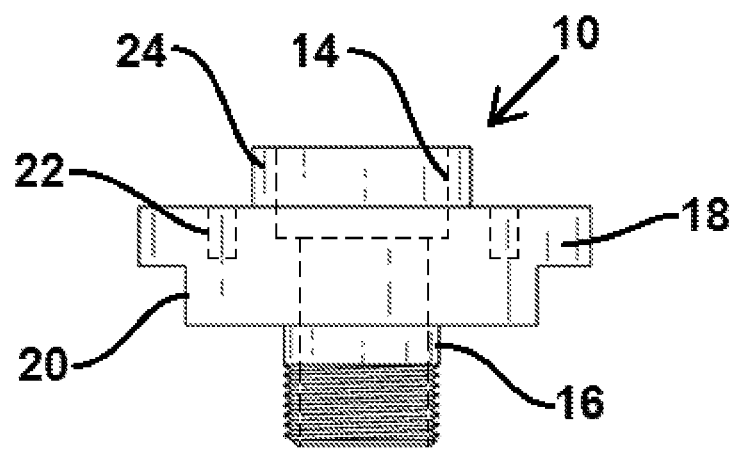
FIG. 5 is a second, opposite side view of the embodiment illustrated in FIG. 3.
Figure 6:
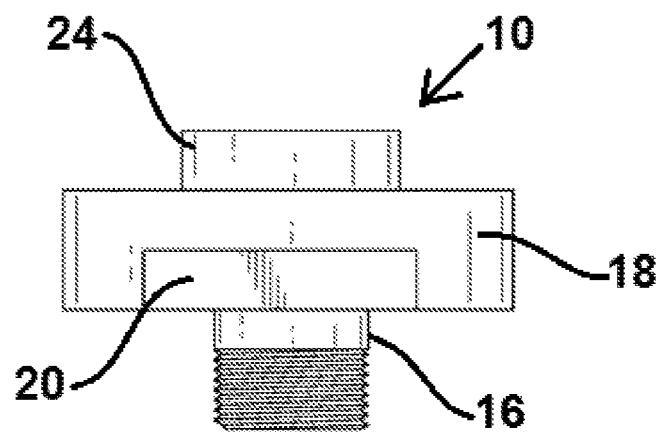
FIG. 6 is a third side view of the embodiment illustrated in FIG. 3 off set 90° from FIG. 4.
Figure 7:
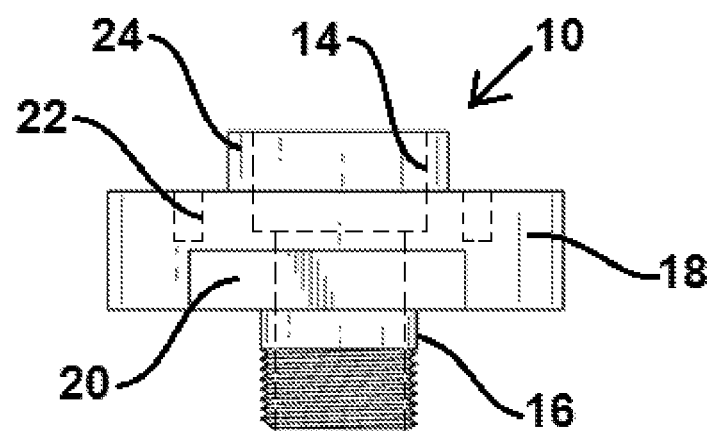
FIG. 7 is a second, opposite side view of the embodiment illustrated in FIG. 6.
Figure 8:
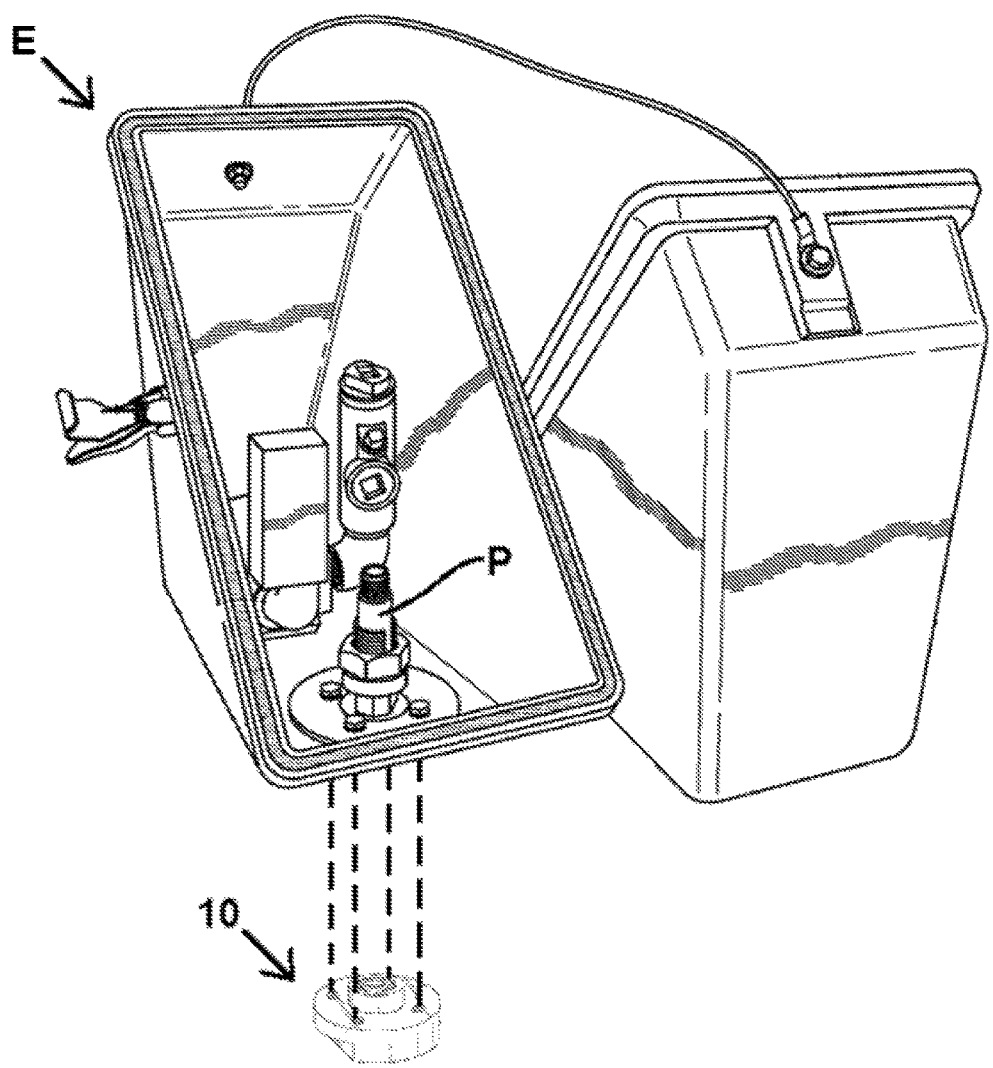
FIG. 8 is an assembly view of the embodiment illustrated in FIG. 1 with a protective enclosure.

FIGS. 1-8 illustrate an embodiment of a disk-like insertion probe adapter 10 for permanently mounting a protective enclosure E thereover and for removably securing a sample extraction insertion probe P to, for example, a natural gas pipeline. The probe adapter 10 of the illustrated embodiment is machined from a single block of non-corrosive material, preferably 316 Stainless Steel.

The probe adapter 10 features an axial feedthrough bore 12 that extends through its center. The top portion of the bore 12 features an interiorly threaded top port 14 for removably receiving and securing the insertion probe P. In this embodiment, the interiorly threaded top port 14 extends axially, entirely through a shoulder 24 of the probe adapter 10 and preferably for a short depth further into the body of a large circular flange 18. The depth in which the top port 14 extends into the body of the flange 18 is any select distance so long as it is not greater than the thickness of the flange 18.

The shoulder 24 protrudes circumferentially upward from the top surface of the flange 18, creating an exterior perimeter about the interiorly threaded top port 14. The shoulder 24 is shaped and dimensioned, ideally to mate with a corresponding opening in the floor of an overlying protective enclosure E to provide both a stronger mechanical and environmentally secure fit to the enclosure E. The height of the projecting shoulder 24 not only serves to increase the relative surface contact area between a mounted probe threadably mated in the top port 14 but also facilitates access to a probe mounted therein by raising a probe tooling engagement area from the housing floor. An increased axial depth of the top port 14 is created by way of the shoulder 24 protruding from the top surface of the flange 18 and provides additional interior surface area for threaded contact with the insertion probe.

A bottom portion 16 of the probe adapter 10 further comprises a pipe fitting with optional exterior threading. Exterior threading at the bottom portion 16 provides for substantially secure mounting of the probe adapter 10 to a pipeline shutoff valve (not illustrated) or the like. In the illustrated embodiment, the top port 14 is of a larger interior diameter than the region of the bore 12 that extends through the bottom portion 16 of the probe adapter 10. Interior diameters of varying sizes for the bore 12 and the top port 14 are likewise contemplated by the present invention.

An embodiment of the probe adapter 10 also features an enlarged circular flange 18 which incorporates a pair of opposing tooling flats 20 (represented by dashed lines) cut out from the lower surface of the flange 18. The pair of opposing tooling flats 20 aid in providing an improved grip by a pipe wrench or other tool on the probe adapter 10 just above the surface of an underlying pipeline. More particularly, the tooling flats 20 provide for secure engagement of a wrench to prevent rotational displacement of the probe adapter 10 while torqueing forces are applied during the removal or tightening of an insertion probe P from the adapter 10 as the probe is treaded or unthreaded from the port 14. Although not as preferred, the adapter 10 may incorporate a single tooling flat 20 to provide similar functionality. That is, a tool is engaged with that single flat 20 at the lower surface of the flange 18 and above the underlying pipe to avoid potentially damaging torqueing forces between the adapter 10 and in the overlying protective enclosure E during manipulation of the associated insertion probe P relative to the adapter 10.

Turning now to secure, permanent mounting of the protective housing to the probe adapter 10, a plurality of spaced threaded housing mounting bolt holes 22 is disposed about the flange 18. While the spacing, placement and number of such bolt holes is a design choice, the illustrated embodiment depicts four such bolt holes 22 equally circumferentially disposed at the same radius about the axis of the probe adapter 10. The bolt holes 22 project axially into the top surface of the flange 18 and are internally threaded. Furthermore, the bolt holes 22 are of a select depth, less than the thickness of the flange 18, and are positioned to receive and secure mounting bolts extending from the floor of the interior of an overlying protective enclosure E, such as a probe housing. Such mounting bolts are used to permanently secure the overlying probe housing to the probe adapter 10 and thereby to the underlying pipeline. By affixing the probe adapter 10 to the underlying pipeline and to the overlying enclosure E, the insertion probe P mounted through the top port 14, is easily removed for repair, inspection, and/or replacement without disturbing the overlying probe housing from its fixed position relative to the pipeline.

An overlying enclosure used in connection with the present invention may be, for example, of the type available from Mustang Sampling LLC of Ravenswood, W. Va. under the name Pony® Heated Probe Enclosure, embodiments of which are described in the respective United States Utility and Design patents U.S. Pat. No. 7,162,933 and D674,052. The Pony® Heated Probe Enclosure, or other similar models, are enclosures designed for environmental isolation of the probe from the ambient environment and may incorporate heater and/or pressure regulating adjuncts associated with the probe itself and or for purposes of extracted sample conditioning. The insertion probes used in connection with the present invention may be of any conventionally available form such as, for example, the Mustang Certiprobe® available from Mustang Sampling LLC, which are used for initial sample extraction from pipelines or other pressure vessels in process sampling.

The adapter of the present invention not only provides the appearance of solidity when the system is assembled but, as stated above, it also offers a functional benefit of facilitating direct access to, and both removal and reinstallation of, an insertion probe without disturbing the mounting of an overlying enclosure.

While not intended to be limiting to relative sizes, an embodiment of the probe adapter of the present invention may feature ¾" male pipe threads on the bottom portion of the probe adapter for the probe adapter to be permanently installed into the top of a pipeline shutoff valve or the like. Similarly, while not intended to be limiting to relative sizes, an embodiment of the invention may also include a top port with ¾" female pipe threads to removably receive and secure an insertion probe with complementary threading. This structure permits the probe to be removable from the adapter without displacing the overlying enclosure. Additional variations that should now be apparent to the skill artisan include, for example, a probe adapter structure that provides a flat upper surface without a shoulder 24 to penetrate the bottom of the overlying protective enclosure E whereby the overlying protective enclosure E sits directly on the entire upper surface of the flange 18. Furthermore, if intended for non-natural gas pipeline use, such as in a chemical processing facility, in lieu of stainless steel, the probe adapter may be fabricated from any of aluminum, high strength ceramics, or other materials suitable for use in connection with other types of pipeline operations.

Although only certain embodiments and variations of the invention have been illustrated in the foregoing specification, it is understood by those skilled in the art that many modifications and embodiments of the invention will come to mind to which the invention pertains, having benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the description of the invention.

I claim:

1. An insertion probe adapter for fluid sample extraction from an underlying pipeline and for mounting of an overlying housing element, comprising:
a body incorporating a pipe mounting flange defining an upper flange surface and a lower flange surface, a pipeline-engaging projecting stem projecting from the lower flange surface for securing the body to the underlying pipeline, a generally axially disposed feedthrough bore for removably retaining an insertion probe engaged therewith axially extending through the depth of the body, the upper flange surface providing an engaging surface for the overlying housing element including at least one fastening member disposed thereon offset from the generally axially disposed feedthrough bore for receiving and retaining the overlying housing element for mounting the housing element thereto; and said lower flange surface including at least one tool engaging flat formed by a cutout along the perimeter thereof; where an insertion probe is removable from the body without disassembling the body from the pipeline and the overlying housing element from the body, by disengaging the probe from the body while engaging a tool with said at least one tooling flat wherein the upper flange surface includes a projecting shoulder defining an upper insertion probe receiving port coaxial with the generally axially disposed feedthrough bore and the shoulder is dimensioned to insert in a complementarily dimensioned opening in a floor of the overlying housing element.

2. The insertion probe adapter according to claim 1, wherein the generally axially disposed feedthrough bore is threaded along at least a portion of the depth.

3. The insertion probe adapter according to claim 2, further comprising a threaded pipe fitting on an exterior of the pipeline-engaging projecting stem projecting below the tooling flat.

4. The insertion probe adapter according to claim 2, wherein the fastening member is a threaded bolt hole positioned to receive and secure at least one mounting bolt extending from an interior of the overlying housing element.

5. The insertion probe adapter of claim 4, wherein the threaded bolt hole extends from the upper flange surface to a select depth less than the thickness of the flange.

6. The insertion probe adapter of claim 5, further comprising a plurality of bolt holes spaced about the upper flange surface.

7. The insertion probe adapter of claim 6, wherein the plurality of bolt holes are equally radially spaced about the generally axially disposed feedthrough bore.

8. The insertion probe adapter of claim 1, further comprising a plurality of square cut tool engaging flats perimetrically spaced about the lower flange surface and having substantially equal cross-sectional dimensions.

9. The insertion probe adapter of claim 1, further comprising a pair of diametrically-spaced, oppositely-facing square cut tool engaging flats.

10. The insertion probe adapter of claim 1, wherein the shoulder extends from the upper flange surface and defines at least a portion of the receiving port.

11. The insertion probe adapter of claim 1, wherein the shoulder is insertable into and mates with the overlying housing element.

12. The insertion probe adapter of claim 11, wherein the body further comprises at least one bolt hole positioned to receive and secure at least one mounting bolt extending from an interior of the overlying housing element.

13. The insertion probe adapter of claim 12, wherein the at least one bolt hole is interiorly threaded.

14. The insertion probe adapter of claim 12, wherein the at least one bolt hole extends from the upper flange surface to a select depth less than the thickness of the body.

15. The insertion probe adapter of claim 1, wherein at least one tool engaging notch is disposed in an edge of the body.

16. A method of removing an insertion probe from a tool-engageable mounting adapter in a protective enclosure from a pipeline where the protective enclosure is mounted to the tool-engageable mounting adapter which is mounted to the pipeline where the tool-engageable mounting adapter features an anti-rotation tool engaging surface, the method comprising the steps of:
  engaging the anti-rotation tool engaging surface of the tool-engageable mounting adapter with a first tool;
  engaging a second tool with the insertion probe in the protective enclosure and applying rotational force thereto relative to the tool-engageable mounting adapter; and
  removing the insertion probe from the tool-engageable mounting adapter while preventing rotation of the tool-engageable mounting adapter relative to the underlying pipeline and overlying protective enclosure.

* * * * *